United States Patent [19]

Keller

[11] Patent Number: 4,815,968
[45] Date of Patent: Mar. 28, 1989

[54] ORTHODONTIC APPLIANCE

[76] Inventor: Duane C. Keller, 62 Grantwood, St. Louis, Mo. 63123

[21] Appl. No.: 118,761

[22] Filed: Nov. 9, 1987

[51] Int. Cl.⁴ ............................................. A61C 7/00
[52] U.S. Cl. ......................................................... 433/7
[58] Field of Search ............................................ 433/7

[56] References Cited

U.S. PATENT DOCUMENTS

| | | | |
|---|---|---|---|
| 1,504,942 | 8/1924 | Comegys | 433/7 |
| 3,162,948 | 12/1964 | Gerber | 433/7 |
| 4,433,956 | 2/1984 | Witzig | 433/7 |

Primary Examiner—Robert Peshock
Attorney, Agent, or Firm—Polster, Polster and Lucchesi

[57] ABSTRACT

An orthodontic appliance is disclosed for expanding (i.e., moving in either inward or outward direction) any desired tooth or teeth of the upper arch, including substantially the entire upper arch relative to a pair of substantially transversely opposed teeth of the upper arch, preferably molars, without reaction forces or moments on this pair of teeth causing unintended movement of these teeth. A band is secured to each tooth of this pair of teeth for mounting a palatal arch bar extending substantially transversely between this pair of teeth. Extension wires extend from the bands for applying corrective forces to any one or more of the teeth of the upper arch spaced from the stated pair of teeth. The arch bar applies a force to a pair of teeth for substantially cancelling out any forces transmitted to the pair of teeth by the expansion wires.

3 Claims, 1 Drawing Sheet

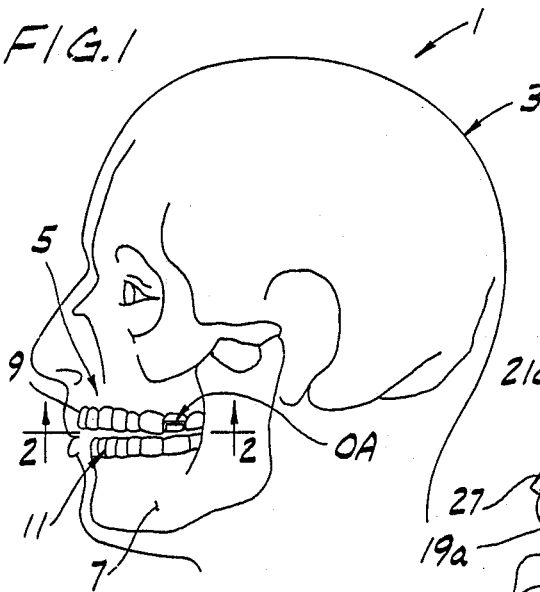
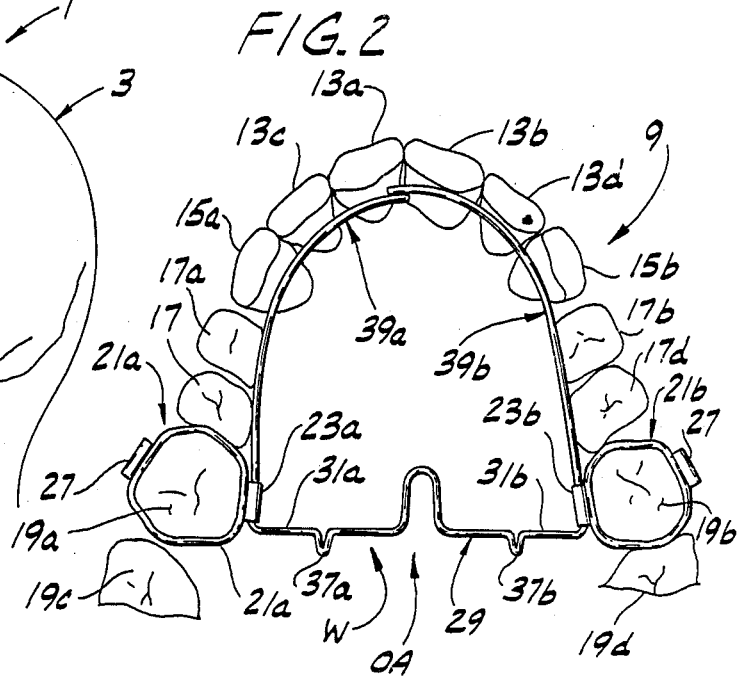
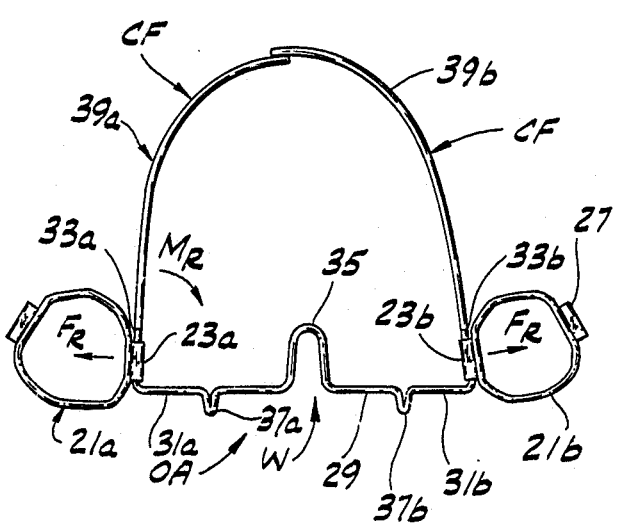
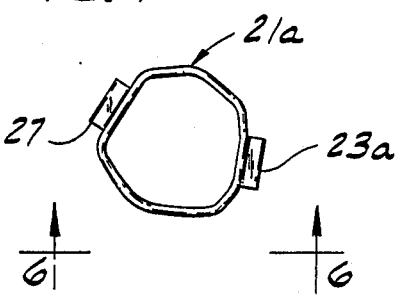
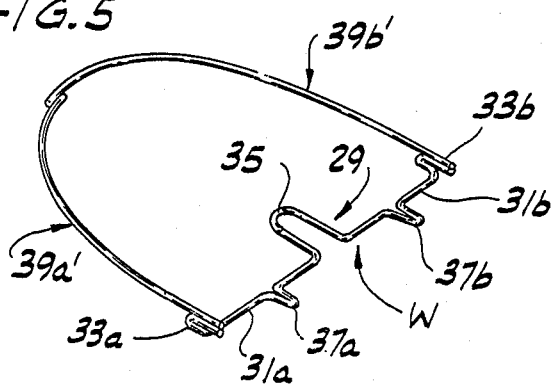
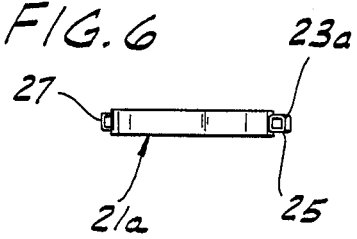

ORTHODONTIC APPLIANCE

BACKGROUND OF THE INVENTION

This invention relates to an orthodontic appliance, and more particularly to an orthodontic appliance for expanding or otherwise moving any desired tooth or teeth of the upper arch, including substantially the entire upper arch.

Generally, orthodontics is a field of dentistry in which the position of the teeth are physically moved relative to one another and relative to the maxilla and mandible, such that after treatment the teeth are in proper relation to one another and to the facial skeletal structure of the patient. Treatment begins by the treating dentist carefully examining the patient's mouth, both visually and radiographically, so as to determine the existing positions of the teeth and the structure of the maxilla and the mandible. The dentist then plans a course of treatment to selectively move certain of the teeth so that after a period of active orthodontic treatment, the teeth will be disposed in a proper positional relationship relative to one another and relative to the patient's facial skeletal structure. The treating dentist has a variety of appliances available for tipping the teeth, rotating them about a longitudinal axis of the tooth, or moving the teeth in posterior, anterior, buccal, or lingual direction. In additional, teeth may be expanded, contracted, intruded, torqued, or de-rotated, as decided by the treating dentist. Generally, existing appliances are available for carrying out each one of these functions on selected teeth of the patient.

Oftentimes, during treatment, it is necessary to expand (or contract) one or more teeth on the patient's arch. Such expansion of the arch is now carried out utilizing appliances referred to as transpalatal expansion appliances.

In addition, it is known that a so-called Crozat appliance may be utilized which has a generally rectangular-shaped crib adapted to be removably fitted over a selected pair of opposed molars on the upper arch. This Crozat appliance has short extensions on it which could be resiliently bent so as to contact an adjacent tooth and to apply a transverse corrective force to the tooth. However, since the Crozat appliance was removable, it did not have a precise fit on the teeth on which it was located, and thus could not repeatedly apply the desired corrective forces. Additionally, the corrective force applied by the Crozat appliance was transmitted to the teeth on which the removable Crozat appliance was attached, thus inducing reactive forces to these teeth, which would cause the teeth on which the appliance is mounted also to move. Since the Crozat appliance is removable, it was impossible to simultaneously utilize fixed bonded or bracketed orthodontic appliances with the Crozat appliance.

Palatal arch bars, such as shown in U.S. Pat. Nos. 3,792,529 and 4,592,725, invented by Robert A. Goshgarian are known in which a band is applied to a selected pair of opposed teeth of the upper arch, typically the patient's maxillary first permanent molars, for derotating, expanding, contracting, intruding, and/or torquing only the first permanent molars to a desired position.

SUMMARY OF THE INVENTION

Among the several objects and features of the present invention may be noted the provision of an orthodontic appliance which may be readily applied to any pair of opposed teeth of the upper arch (preferably a pair of opposed molars), which may apply, via an expansion wire, either an expansive or contractive force on any one or all of the teeth of the upper arch, and which substantially cancels any reaction forces applied to the pair of teeth on which the appliance is mounted resulting from the corrective forces applied to the desired teeth to be corrected thereby to substantially eliminate the effects of unintended positional forces applied to the teeth carrying the appliance;

The provision of such an orthodontic appliance which does not substantially interfere with the patient's ability to speak or to chew;

The provision of such an appliance in which a portion of the appliance extending transversly between a pair of opposed teeth and extending in posterior or anterior direction toward the teeth to be moved may be readily removed and reinstalled by the patient;

The provision of such an appliance which may be readily adjusted so as to increase or decrease the corrective and reactive forces;

The provision of such an orthodontic appliance that can move one tooth of the upper arch or substantially the entire arch at a relatively great distance from the teeth on which it is mounted;

The provision of such an appliance fitted to the upper arch which permits the simultaneous treatment of the temporomandibular joint (TMJ), as described in my U.S. Pat. No. 4,468,196;

The provision of such an appliance which may be utilized not only to expand a desired tooth or teeth of the upper arch, but may also be used to contract teeth of the upper arch;

The provision of such an appliance which allows the simultaneous usage of fixed bonded or bracketed orthodontic appliances;

The provision of such an appliance which will augment bodily movement of a selected tooth (or selected teeth) with precise fixed bonded or bracketed orthodontic appliances when orthodontic movements are complete: and The provision of such an orthodontic appliance which is relatively easy to install, which may be comfortably worn by the patient for extended periods of time, and which permits the treating dentist wide flexibility in the course of treatment.

Other objects and features of this invention will be in part apparent and in part pointed out hereinafter.

Briefly stated, an orthodontic appliance of the present invention is provided for expanding any desired tooth or teeth of the upper arch, including substantially the entire upper arch, relative to a pair of substantially transversely opposed teeth, preferably molars, of the upper arch without reaction forces on the pair of teeth to which the appliance is attached causing unintended movement of this pair of teeth. The appliance comprises mounting means secured to this pair of teeth. Expansion wires extend from the mounting means for applying expansive, corrective forces to any one or more of the teeth of the upper arch. A palatal arch bar extends substantially transvesely between this pair of teeth for applying a force to the pair of teeth so as to substantially cancel out reaction forces transmitted to the pair of teeth by the expansion wires.

BRIEF DESCRIPTION OF THE DRAWINGS

FIG. 1. is a left side elevational view of a typical patient's head, illustrating the main anatomical and skeletal features of the patient's head and jaw, with the orthodontic appliance of the present invention installed on the patient's upper arch;

FIG. 2 is a view taken along line 2—2 of FIG. 1, illustrating the teeth of the upper jaw of the patient (i.e., the upper arch) with an orthodontic appliance of the present invention installed on the upper arch;

FIG. 3 is a view similar to FIG. 2, with the orthodontic appliance removed from the upper arch;

FIG. 4 is a view of a band securable to a selective tooth for mounting the appliance of the present invention;

FIG. 5 is a perspective view of the appliance removed from the mounting bands, showing a transversely extending palatal arch bar and anteriorly extending expansion wires; and FIG. 6 is a side elevational view, taken along line 6—6 of FIG. 4, illustrating, in a greater scale, a socket carried on the inner (or lingual) side of the band for receiving and mounting the orthodontic appliance therein.

Corresponding reference characters indicate corresponding parts throughout the several views of the drawings.

DESCRIPTION OF A PREFERRED EMBODIMENT

Referring to FIG. 1, a patient's head, as generally indicated at 1, is illustrated. The head includes a skull 3 which may be divided into two main sections or parts, namely, the cranium and the skeleton of the face. The facial skeleton includes the maxilla 5 in which the teeth of the upper jaw, constituting the patient's upper arch, are embedded, and the mandible 7 in which the teeth of the lower jaw (i.e., the lower arch) are embedded. The upper arch is indicated by reference character 9 and the upper arch is indicated by reference character 11.

As shown in FIG. 2, the upper arch 9 is generally symmetric and includes four incisors, 13a–13d, a pair of opposed canine teeth 15a, 15b, two pairs of pre-molars 17a, 17b and 17c, 17d, and two pairs of molars 19a, 19b and 19c, 19d. It will be appreciated that, in FIG. 2, the third molars are not shown.

In accordance with this invention, an orthodontic appliance, as indicated in its entirety OA, is affixed to a selected pair of opposed teeth, for example, molars 19a, 19b, of upper arch 9 for expanding (or contracting) any desired tooth or teeth of the upper arch, including the entire upper arch (except for the teeth on which the orthodontic appliance is mounted) relative to the pair of opposed teeth on which the appliance is mounted without causing unwanted movement of this pair of teeth 19a, 19b. More specifically, orthodontic appliance OA comprises a pair of bands 21a, 21b affixed to the respective pair of opposed molars 19a, 19b, as illustrated in FIG. 2. Each of the bands 21a, 21b has a respective inner or lingual socket 23, having a respective socket opening 25 therein, as best shown in FIG. 6. This lingual attachment is designed to receive the threaded lingual wire, as my U.S. Pat. No. 4,468,196, as well as the transpalatal arch wire of the instant invention. These socket openings 25 are preferably tapered from front to rear to facilitate placement of the appliance thereby making it easier for patients to remove and reinsert the appliances in the brackets. An optional buccal (outer) socket 27 may be provided on bands 21a, 21b for receiving an outer or buccal arch wire (not shown) which in turn may be adhesively bonded to selected pads (also not shown) cemented to the buccal faces of the teeth. For greater detail of the construction and purpose of the threaded lingual wire and the buccal arch wire, reference may be made to my U.S. Pat. No. 4,468,196, which is herein incorporated by reference.

In accordance with this invention, orthodontic appliance OA includes a palatal arch bar or wire, as generally indicated at 29, constituting means for applying a force to the above-noted pair of teeth 19a, 19b for substantially cancelling out any reaction forces transmitted to this pair of teeth by the orthodontic appliance as it applies a corrective force CF to the selected tooth or teeth of the upper arch 9 being expanded or contracted. This palatal arch bar 29 may, for example, be similar to the palatal arch bars disclosed in the above-noted U.S. Pat. Nos. 3,792,529 and 4,592,725, which both are herein incorporated by reference.

More specifically, arch bar 29 is made of wire W, which is preferably a resilient, tough, stainless steel wire which may be readily bent on itself, in the manner illustrated in FIGS. 3 and 5, so as to form the various parts of the arch bar, which will now be described. More specifically, arch bar 29 includes outer wire body portions 31a, 31b at each transverse side thereof. The outer terminal ends 33a, 33b of the wire body portions 31a, 31b, respectively, are snuggly received or socketed in socket openings 25 of respective inner sockets 23a, 23b. Further, a generally U-shaped loop, as indicated at 35, is provided between the wire body portion 31a, 31b, which may be readily formed by the treating dentist, either to spread or compress the palatal arch bar thereby to create force in a desired direction on bands 21a, 21b, which in turn applies a desired force to the teeth 19a, 19b on which the bands are mounted. Optional spurs 37a, 37b are provided midway along body portions 31a, 31b, which may be utilized as attachments for rubber bands, referred to lingual elastics, for other orthodontic treatment which does not, per se, constitute a part of this invention, and thus a detailed description of this is not incorporated herein. However, for a better discussion of the use of these lingual elastics, reference may be made to the above-noted Goshgarian U.S. Pat. No. 4,592,725.

Still further in accordance with this invention, socalled expansion wires, as indicated generally at 39a, 39b, are cantilevered from respective terminal ends 33a, 33b of arch bar 29 in such manner that the expansion wires extend from the terminal ends in either anterior (as illustrated in FIG. 2) or in posterior (not shown) direction from the pair of teeth 19a, 19b of the upper arch 9 on which the orthodontic appliance OA is mounted for applying a predetermined expansive, corrective force to any one or more of the teeth of the upper arch 9 which are spaced from the pair of teeth 19a, 19b. It will be understood that, within the broader aspects of this invention, the term "expansive, corrective force" need not be limited to forces which expand the selected teeth of the upper arch, but may be utilized to contract the upper arch as well. For example, in accordance with this invention, expansion wires (not shown) may also be received in the optional buccal sockets 27 on the outside of teeth 19a, 19b, and the wires may be bent into selective engagement with the buccal faces of one or more teeth of the upper arch so as to apply a compressive force to the selective tooth or teeth of the arch thereby to compress or otherwise move these teeth.

In use, if a treating dentist determines, for example, that incisor 13c, canine 15a, and pre-molar 17a must be expanded outwardly, and if corresponding incisor 13d, canine 15b, and pre-molar 17b must also be expanded outwardly, bands 21a, 21b may be securely fitted to a selected pair of opposed teeth, such as molars 19a, 19b. Orthodontic appliance OA is then inserted into socket openings 25 of sockets 23a, 23b such that the expansion wires 39a, 39b are disposed on the lingual or inner faces of the teeth of the upper arch. The expansion wires 39a, 39b are then bent in such manner as to resiliently engage the lingual faces of the desired teeth to be expanded, and to exert a desired correctional force on each of the teeth.

As shown in FIG. 3, an equal and opposite force CF is exerted on the expansion wires 39a, 39b by the teeth being corrected. This expansion force results, at the location of sockets 23 on bands 21a and 22b, a reaction force $F_R$, and a reaction moment $M_R$ on teeth 19a, 19b. It will be appreciated that by expanding or contracting the U-shaped loop 35 of arch bar 29, by appropriately bending body portions 31a, 31b of wire W, and further by bending terminal ends 33a, 33b relative to the wire body portions 31a, 31b, appropriate counteractive forces and moments can be induced into band 21a, 21b by the arch bar so as to substantially cancel out the effects of the reactive and corrective forces CF and moments $M_R$ applied on expansion wires 39a, 39b by the teeth being expanded. In this manner, the net forces and moments applied to the anchoring teeth 19a, 19b by expansion wires 39a, 39b are essentially cancelled out, and thus the corrective forces applied to the desired teeth in the upper arch have little or no adverse effect on the anchoring teeth 19a, 19b.

Further in accordance with this invention, the orthodontic appliance OA of the present invention heretofore described may be used simultaneously with and in conjunction with my earlier appliance, as described in detail in my U.S. Pat. No. 4,468,196 (herein incorporated by reference). Specifically, the appliance OA described herein may be applied to the upper arch 9, as shown in FIG. 2, and the appliance of my U.S. Pat. No. 4,468,196 may be applied to the upper arch, as shown in FIG. 3 of my U.S. Pat. No. 4,468,196, such that appliance OA herein and the appliance of my earlier patent may simultaneously be used to expand the upper arch and to carry out a course of orthodontic and orthopedic treatment of the temporomandibular joint (TMJ) without the two appliances interfering with one another and permitting the patient to speak and chew without undue difficulty.

In view of the above, it will be seen that the other objects of this invention are achieved and other advantageous results obtained.

As various changes could be made in the above constructions without departing from the scope of the invention, it is intended that all matter contained in the above description or shown in the accompanying drawing shall be interpreted as illustrative and not in a limiting sense.

What is claimed is:

1. An orthodontic appliance for expanding any desired tooth or teeth of the upper arch, including substantially the entire upper arch, relative to a pair of substantially transversely opposed teeth of the upper arch, preferably molars, without reaction forces on said pair of teeth causing unintended movement of said pair of teeth, said appliance comprising means for mounting said appliance to a pair of opposed teeth of said upper arch, expansion wires extending from said mounting means for applying corrective forces to any one or more of the teeth of said upper arch, and a removable palatal arch bar also extending from said mounting means substantially transversely between said pair of teeth for applying a force to said pair of teeth so as to substantially cancel out reaction forces transmitted to said pair of teeth by said expansion wires said arch bar being of a resilient, bendable material which may be selectively shaped so as to apply reactive forces to said mounting means for cancelling out said reaction forces transmitted to said pair of teeth by said expansion wires.

2. An orthodontic appliance as set forth in claim 1 wherein each of said expansion wires is secured to a respective said mounting means and is disposed on the sides of said upper arch for contacting said one or more teeth of said upper arch and for applying said corrective forces thereto.

3. An orthodontic appliance as set forth in claim 1 wherein said arch bar includes wire body portions, and further having terminal ends at each end of said wire body portions, said wire body portions being selectively bendable along their length so as to apply desired reactive forces to said mounting means, and said terminal means being bendable relative to said body portions such that when said terminal end portions are received in said mounting means, said palatal arch bar applies both desired corrective forces and corrective moments to said mounting means thereby to substantially cancel out reaction forces and transmitted to said pair of teeth by said expansion wires.

* * * * *